(12) United States Patent
Fraser et al.

(10) Patent No.: US 11,673,135 B2
(45) Date of Patent: Jun. 13, 2023

(54) FLUID PORT

(71) Applicant: Global Life Sciences Solutions USA LLC, Marlborough, MA (US)

(72) Inventors: Donald M. Fraser, Marlborough, MA (US); Yasser Ali, Marlborough, MA (US); Mathew Wecharatana, Marlborough, MA (US); James Brueggeman, Marlborough, MA (US)

(73) Assignee: GLOBAL LIFE SCIENCES SOLUTIONS USA LLC, Marlborough, MA (US)

(*) Notice: Subject to any disclaimer, the term of this patent is extended or adjusted under 35 U.S.C. 154(b) by 61 days.

(21) Appl. No.: 16/955,173

(22) PCT Filed: Dec. 14, 2018

(86) PCT No.: PCT/EP2018/085066
§ 371 (c)(1),
(2) Date: Jun. 18, 2020

(87) PCT Pub. No.: WO2019/121424
PCT Pub. Date: Jun. 27, 2019

(65) Prior Publication Data
US 2020/0316584 A1    Oct. 8, 2020

Related U.S. Application Data

(60) Provisional application No. 62/609,014, filed on Dec. 21, 2017.

(51) Int. Cl.
*B01L 3/00*       (2006.01)
*C12M 1/00*       (2006.01)

(52) U.S. Cl.
CPC ............. *B01L 3/502* (2013.01); *C12M 23/14* (2013.01); *B01L 2200/026* (2013.01); *B01L 2200/0689* (2013.01); *B01L 2300/0681* (2013.01)

(58) Field of Classification Search
CPC ............... B01L 3/502; B01L 2200/026; B01L 2200/0689; B01L 2300/0681;
(Continued)

(56) References Cited

U.S. PATENT DOCUMENTS

| 4,611,974 A | 9/1986 | Holland |
| 2003/0036192 A1* | 2/2003 | Singh ............... B01F 31/23 435/297.2 |

(Continued)

FOREIGN PATENT DOCUMENTS

| CN | 1894528 A | 1/2007 |
| CN | 101687581 A | 3/2010 |

(Continued)

OTHER PUBLICATIONS

PCT International Search Report and Written Opinion for PCT Application No. PCT/EP2018/085066 dated Mar. 18, 2019 (7 pages).

(Continued)

*Primary Examiner* — Benjamin R Whatley
*Assistant Examiner* — Jacqueline Brazin
(74) *Attorney, Agent, or Firm* — Eversheds Sutherland (US) LLP

(57) ABSTRACT

The present invention relates to a flexible bag, a perfusion filter and a fluid port. The fluid port comprises: —a first fluid connection (3; 3'); —a second fluid connection (5; 5') being in fluid communication with the first fluid connection (3; 3'); —an intermediate fluid path (7: 7') connecting the first fluid connection (3; 3') with the second fluid connection (5; 5');

(Continued)

wherein said intermediate fluid path (7; 7') at least a portion of which comprises a substantially right-angled bend (9; 9'); —a protection cap (11; 11') protecting at least the bend (9; 9') of the intermediate fluid part (7; 7') from contact with other objects; and —a connection surface (13; 13') configured for sealing to a film of an object to be supplied by said port, said connection surface will, when sealed to the film of the object, together with the film provide a fluid tight seal surrounding the first fluid connection (3; 3').

14 Claims, 4 Drawing Sheets

(58) Field of Classification Search
CPC ...... C12M 23/14; C12M 27/16; C12M 29/04; C12M 21/00; C12M 21/08
USPC ...................................................... 435/297.1
See application file for complete search history.

(56) References Cited

U.S. PATENT DOCUMENTS

| | | | |
|---|---|---|---|
| 2006/0240546 A1* | 10/2006 | Goodwin | C12M 23/00 435/289.1 |
| 2007/0010791 A1 | 1/2007 | Drechsler et al. | |
| 2010/0140182 A1* | 6/2010 | Chapman | B01D 21/262 210/741 |
| 2011/0151552 A1* | 6/2011 | Jiang | C12M 27/16 435/289.1 |
| 2015/0118753 A1 | 4/2015 | Brau et al. | |
| 2017/0276666 A1* | 9/2017 | Lyons | C12M 35/04 |

FOREIGN PATENT DOCUMENTS

| | | | |
|---|---|---|---|
| CN | 101821007 | A | 9/2010 |
| CN | 103764187 | A | 4/2014 |
| JP | 2007514910 | A | 6/2007 |
| JP | 2008507912 | A | 3/2008 |
| JP | 2008536525 | A | 9/2008 |
| WO | 005068882 | A1 | 7/2005 |
| WO | 2006116069 | A1 | 2/2006 |
| WO | 2017/055059 | A1 | 4/2017 |

OTHER PUBLICATIONS

Office Action Issued in Japanese Patent Application No. 2020-534550, dated Oct. 11, 2022 with English Translation. (10 pages).
Chinese Office Action for CN Application No. 201880082386.1, dated Feb. 3, 2023 with English Translation (8 pages).
Chinese Office Action for CN Application No. 2020-534550, dated Feb. 27, 2023 with English Translation (8 pages).

* cited by examiner

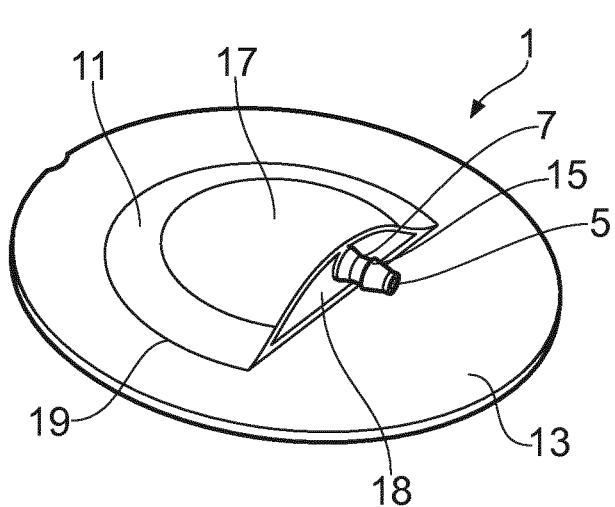
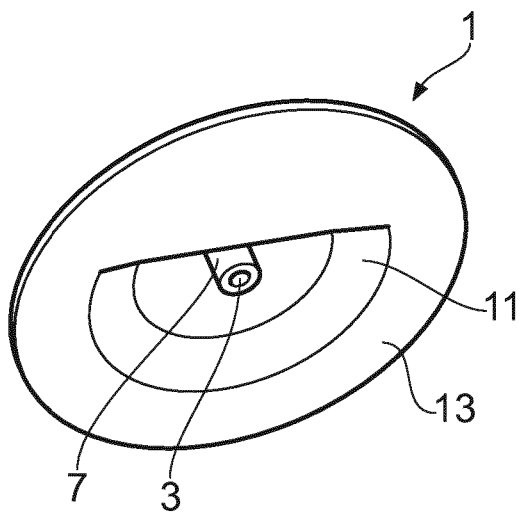
FIG. 1a
FIG. 1b
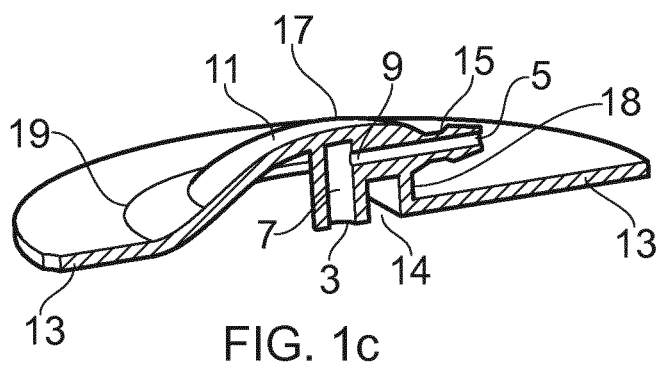
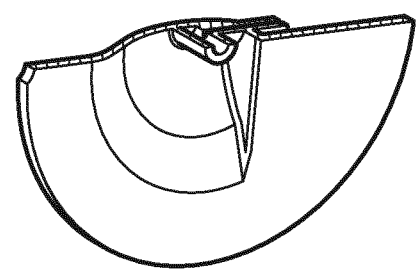
FIG. 1c
FIG. 1e
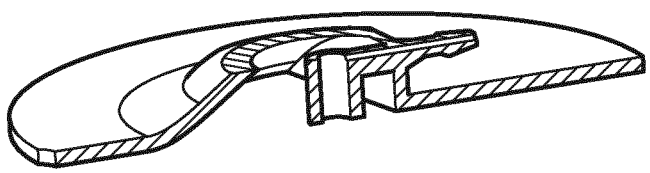
FIG. 1d

FLUID PORT

CROSS REFERENCE TO RELATED APPLICATIONS

This application claims the priority benefit of PCT/EP2018/085066 filed on Dec. 14, 2018, which claims priority benefit of U.S. Provisional Patent Application No. 62/609,014 filed on Dec. 21, 2017, the entire contents of which are hereby incorporated by reference herein.

TECHNICAL FIELD OF THE INVENTION

The present invention relates to a fluid port and to a perfusion filter and to a flexible bag.

BACKGROUND OF THE INVENTION

When a direction of a flow need to be changed an elbow connector can be provided to a port. However, for example in flexible bags such elbow connectors can cause problems, for example during assembly, transport and storage when walls of the flexible bag may be pushed against the elbow connector. The walls may be dented or even ruptured by the connector.

Typically a perfusion filter used in a bioreactor bag is connected by an elbow connector and problems may arise during transport and storage as described above.

SUMMARY

An object of the present invention is to provide an improved fluid port.

A further object of the invention is to provide an improved perfusion filter.

A further object of the invention is to provide an improved flexible bag.

A further object of the invention is to reduce the risk for damage to walls of a flexible bag when the bag is transported or stored.

A further object of the invention is to provide a fluid port which can deflect the fluid flow while not causing damage to objects around.

This is achieved in a fluid port, in a perfusion filter and in a flexible bag according to the independent claims.

According to one aspect of the invention a fluid port is provided comprising:
 a first fluid connection;
 a second fluid connection being in fluid communication with the first fluid connection;
 an intermediate fluid path connecting the first fluid connection with the second fluid connection; wherein said intermediate fluid path at least a portion of which comprises a substantially right-angled bend;
 a protection cap protecting at least the bend of the intermediate fluid part from contact with other objects; and
 a connection surface configured for sealing to a film of an object to be supplied by said port, said connection surface will, when sealed to the film of the object, together with the film provide a fluid tight seal surrounding the first fluid connection.

Hereby a fluid port is provided with an inherent fluid deflection, i.e. fluid flow into the fluid port will be provided in a direction which is substantially perpendicular to a fluid flow out from the fluid port. Furthermore the fluid port comprises a protection cap which will protect at least the bent part of the fluid port from providing damage to objects around, for example if a flexible bag is pushed down onto the fluid port the protection cap will distribute the pressure to a larger and smoother surface. Furthermore the connection surface of the fluid port can be sealed directly to a film of the object to which the port should be connected. Hereby an extra port for changing the direction of the flow is avoided. This eliminates an assembly operation and potential leak point between two components.

According to another aspect of the invention a perfusion filter comprising such a fluid port is provided. Wherein said connection surface of the fluid port is sealed to an outer film of the perfusion filter, wherein an opening is provided in the outer film of the perfusion filter inside the fluid tight seal surrounding the first fluid connection such that the opening mates with the first fluid connection.

Hereby a perfusion filter having a port with inherent fluid deflection, substantially 90 degrees is provided. Said fluid port will furthermore not cause damage to objects provided near. For example if the perfusion filter is provided inside a flexible bag, for example a bioreactor, said flexible bag can be transported and stored, may be many bags on top of each other, without the risk that walls of the flexible bag are dented or ruptured by the fluid port of the perfusion filter. The avoidance of the use of an extra elbow port for changing flow direction is advantageous because it eliminates an assembly operation and a potential leak point.

According to another aspect of the invention a flexible bag comprising such a perfusion filter is provided. Hereby there is a decreased risk of denting or rupture of walls of the flexible bag when they are transported or stored, may be stacked on each other.

According to another aspect of the invention a flexible bag comprising such a fluid port is provided wherein the connection surface of the fluid port is sealed to a wall of the flexible bag and wherein an opening is provided through the wall inside the surrounding seal for allowing access to the first fluid connection of the fluid port.

Hereby a deflection of the fluid flow can be provided without the need of an additional component.

In one embodiment of the invention the connection surface of the fluid port is connected to one or more of the other parts of the fluid port such that when a seal surrounding the first fluid connection is provided between the connection surface and the film of the object to which the fluid port should be connected the first fluid connection is only accessed through an opening in the film provided within the surrounding seal.

In one embodiment of the invention the protection cap is configured for protecting at least the bend of the intermediate fluid path from contact with objects approaching the fluid port from a side of the fluid port being opposite the side where the first fluid connection is provided.

In one embodiment of the invention a barb is provided to the intermediate fluid path towards the second fluid connection, such that a tube can be connected to the second fluid connection of the fluid port.

In one embodiment of the invention the connection surface is connected to the protection cap and said protection cap is formed as a part of a dome, wherein a top position of said protection cap is provided above the bend of the intermediate fluid path and an outer periphery of the protection cap is connected to the connection surface.

In one embodiment of the invention both the protection cap and the connection surface are formed as planar discs which are provided with the same orientation but in different planes, wherein said intermediate flow path is provided in between the protection cap and the connection surface and the intermediate flow path is connected to the protection cap and the connection surface.

BRIEF DESCRIPTION OF THE DRAWINGS

FIG. 1a shows schematically a perspective top view of a fluid port according to one embodiment of the invention.

FIG. 1b shows schematically a perspective bottom view of the same fluid port as shown in FIG. 1a.

FIGS. 1c, 1d and 1e are cross sections from different views of the same fluid port 1 as shown in FIGS. 1a and 1b.

DETAILED DESCRIPTION OF EMBODIMENTS

Figure 2:
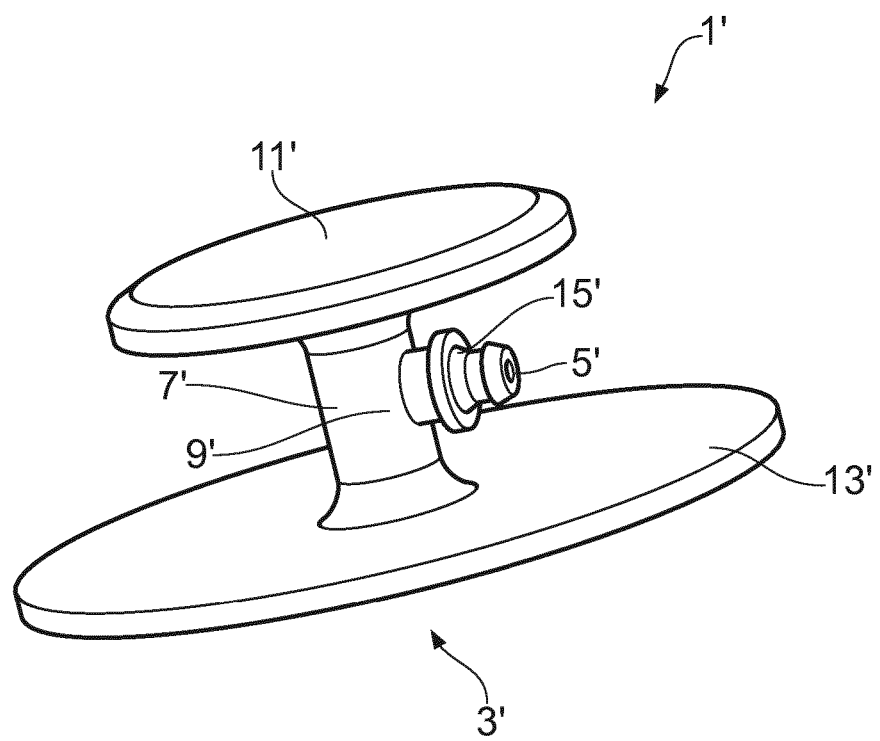
FIG. 2 shows schematically a perspective view of a fluid port according to another embodiment of the invention.

FIG. 1a shows schematically a perspective top view of a fluid port 1 according to one embodiment of the invention. FIG. 1b shows schematically a perspective bottom view of the same fluid port 1 as shown in FIG. 1a. FIGS. 1c, 1d and 1e are cross sections from different views of the same fluid port 1 as shown in FIGS. 1a and 1b. The fluid port 1 comprises a first fluid connection 3, a second fluid connection 5 which is in fluid communication with the first fluid connection 3 and an intermediate fluid path 7 connecting the first fluid connection 3 with the second fluid connection 5. The direction of fluid flow through the fluid port 1 can change and the first fluid connection 3 can be both a fluid inlet and a fluid outlet depending on how the fluid port 1 is used. Said intermediate fluid path 7 comprises a substantially right-angled bend 9. Hereby a fluid flow provided into the first fluid connection 3 of the fluid port 1 will have a direction being substantially perpendicular to a fluid flow provided out from said fluid port 1 through the second fluid connection 5. The fluid port 1 comprises further a protection cap 11 protecting at least the bend 9 of the intermediate fluid part 7 from contact with other objects. The bend of a conventionally used elbow connector can cause damage to nearby objects, for example to a wall of a flexible bag. The protection cap 11 according to the invention is provided for reducing this risk. The protection cap 11 is configured for protecting at least the bend 9 of the intermediate fluid path 7 from contact with objects approaching the fluid port 1 from a side of the fluid port being opposite the side where the first fluid connection 3 is provided. The protection cap 11 will distribute a pressure from a nearby object to a larger and smoother surface.

Furthermore the fluid port 1 comprises a connection surface 13 configured for sealing to a film of an object to be supplied by said port. Said connection surface 13 will, when sealed to the film of the object, together with the film provide a fluid tight seal surrounding the first fluid connection 3. In the embodiment as shown in FIGS. 1a-1e the connection surface 13 has an outer circular form and it comprises a central opening 14 for the first fluid connection 3.

The connection surface 13 of the fluid port 1 is connected to one or more of the other parts of the fluid port 1 such that when a seal surrounding the first fluid connection 3 is provided between the connection surface 13 and the film of the object to which the fluid port 1 should be connected the first fluid connection 3 is only accessed through an opening in the film provided within the surrounding seal. In this embodiment of the invention the connection surface 13 is connected to the protection cap 11 and the protection cap 11 is formed as a part of a dome. A top position 17 of said protection cap 11 is provided above the bend 9 of the intermediate fluid path 7 and an outer periphery 19 of the protection cap 11 is connected to the connection surface 13. This part of a dome will provide a smooth surface to the fluid port 1 thereby reducing the risk that a nearby object will be damaged. The dome is not a complete dome with a circular outer periphery but has instead a cut edge 18 just after the top position 17. Hereby the intermediate fluid path 7 will protrude out through this cut edge 18 towards the second fluid connection 5. A barb 15 is provided to the intermediate fluid path 7 towards the second fluid connection 5, such that a tube can be connected to the second fluid connection 5 of the fluid port 1. The barb 15 will project out from the protection cap 11 in a direction being substantially perpendicular to a direction of a fluid flow entering the first fluid connection 3.

FIG. 2 shows schematically a perspective view of a fluid port 1' according to another embodiment of the invention. The fluid port 1' comprises also in this embodiment a first fluid connection 3', a second fluid connection 5' which is in fluid communication with the first fluid connection 3' and an intermediate fluid path 7' connecting the first fluid connection 3' with the second fluid connection 5'. Said intermediate fluid path 7' comprises a substantially right-angled bend 9'. Hereby a fluid flow provided into the first fluid connection 3' of the fluid port 1' will have a direction being substantially perpendicular to a fluid flow provided out from said fluid port 1' through the second fluid connection 5'. The fluid port 1' comprises further a protection cap 11' protecting at least the bend 9' of the intermediate fluid part 7' from contact with other objects. The protection cap 11' is configured for protecting at least the bend 9' of the intermediate fluid path 7' from contact with objects approaching the fluid port 1' from a side of the fluid port being opposite the side where the first fluid connection 3' is provided. The protection cap will distribute the pressure to a larger and smoother surface.

Furthermore the fluid port 1' comprises a connection surface 13' configured for being able to seal to a film of an object to which said fluid port 1' should be provided. Said connection surface 13' will, when sealed to the film of the object, together with the film provide a fluid tight seal surrounding the first fluid connection 3'. In the embodiment as shown in FIG. 2 the connection surface 13' has a circular planar form. The form does not necessarily need to be circular but can be any other form. A central opening 14' is provided in the connection surface 13' mating with the first fluid connection 3'.

The connection surface 13' of the fluid port 1' is connected to the inlet 3' of the fluid port 1' such that when a seal surrounding the first fluid connection 3' is provided between the connection surface 13' and the film of the object to which the fluid port 1' should be connected the first fluid connection 3' is only accessed through an opening in the film provided within the surrounding seal. In this embodiment of the invention both the protection cap 11' and the connection surface 13' are formed as planar discs which are provided in the same orientation but in different planes, wherein said intermediate flow path 7' is provided in between the protection cap 11' and the connection surface 13' and the intermediate flow path 7' is connected to the protection cap 11' and the connection surface 13'.

Figure 3:
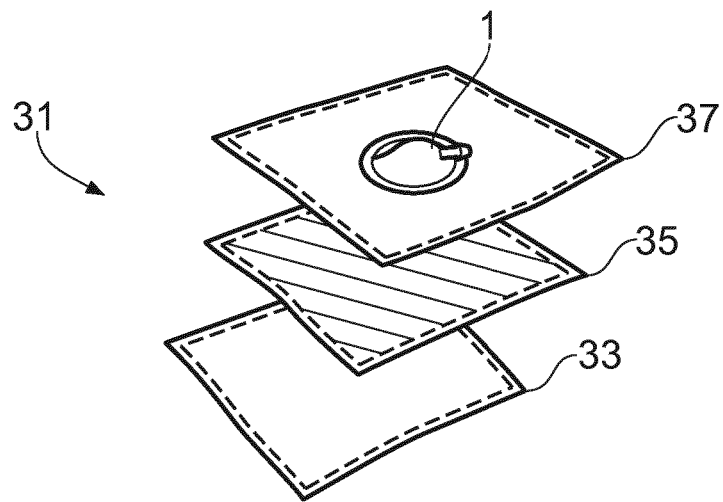
FIG. 3 shows schematically the different layers of a perfusion filter. The top layer of the perfusion filter comprises a fluid port according to one embodiment of the invention.

FIG. 3 shows schematically a perfusion filter 31 with its different layers separated. This perfusion filter 31 is provided with a fluid port 1 according to one embodiment of the invention. The perfusion filter 31 comprises three layer: a bottom layer, which is a filter membrane 33, a middle layer, which is a mesh 35 and a top layer, which can be an EVA film 37. The top layer 37 can also be Bioclear 10, Bioclear 11 or Fortem. The three layers are sealed together. The fluid port 1 is provided to the top layer 37. Such a perfusion filter 31 can be used in a flexible bag being a bioreactor. The perfusion filter 31 is used for filtering out waste from a cell culture in the bioreactor. This is shown in FIG. 4.

Figure 4:
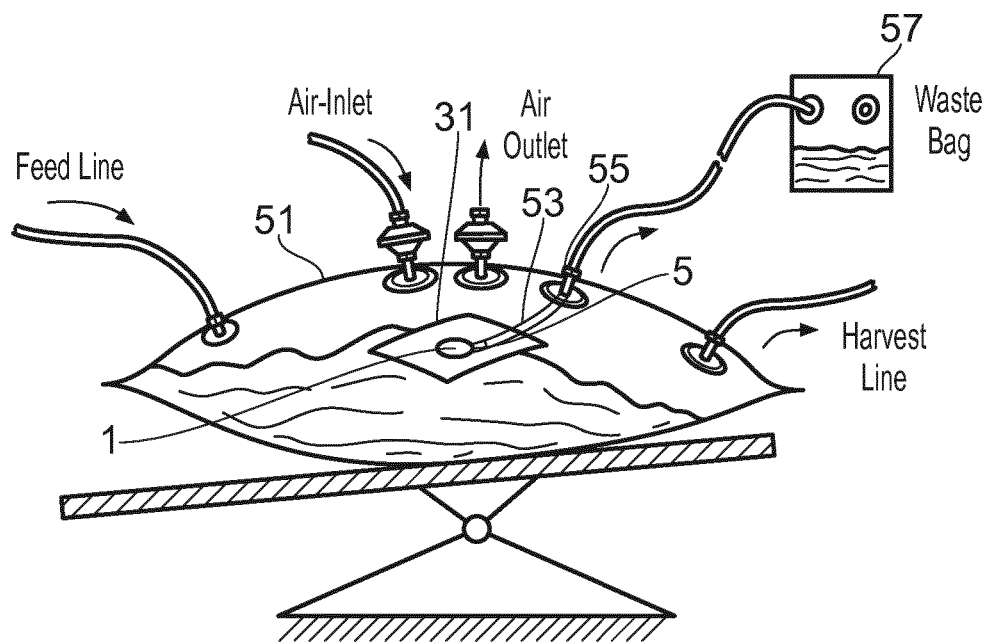
FIG. 4 shows schematically a flexible bag comprising a perfusion filter comprising a fluid port according to one embodiment of the invention.

FIG. 4 shows schematically a flexible bag 51 comprising a perfusion filter 31 comprising a fluid port 1 according to one embodiment of the invention. The perfusion filter 31 is floating in the cell culture in the flexible bag 51. The fluid port 1 according to the invention is connected by its second fluid connection 5 by a tubing 53 to a port 55 in a wall of the flexible bag 51 and further by tubing to a waste bag 57. The connection surface 13 of the fluid port 1 has been sealed to the top layer 37 of the perfusion filter 31 and an opening in the top layer 37 will mate with the first fluid connection 3 of the fluid port 1 such that waste from the cell culture can be filtered out through the perfusion filter 31 and further through the fluid port 1 out to the waste bag 57. In prior art such a perfusion filter comprises a conventional port to which a conventional elbow connector is attached. With a conventional elbow connector provided inside a flexible bag there is a risk that the walls of the flexible bag get damaged when they come into contact with the elbow connector as discussed above. The fluid port 1 according to the invention is advantageous both because it provides the protection cap 11 protecting for example the walls of the flexible bag from getting damaged and because it is an integrated fluid port of the perfusion filter which port deviates the flow substantially 90 degrees like an elbow connector, i.e. an extra port for deviating the flow is avoided.

Figure 5:
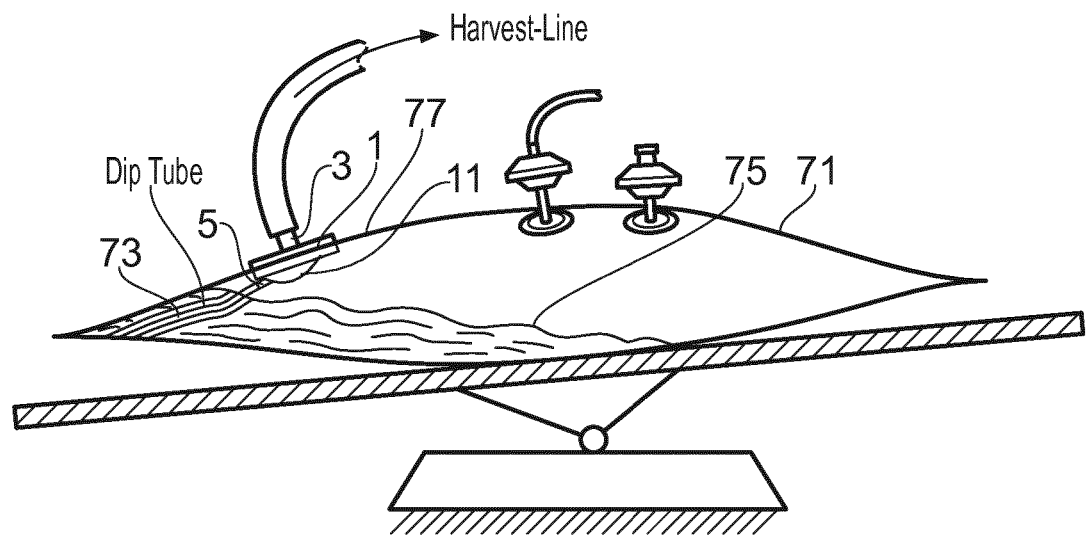
FIG. 5 shows schematically a flexible bag comprising a dip tube inside the bag, wherein said dip tube is connected to the outside of the flexible bag by a fluid port according to one embodiment of the invention.

FIG. 5 shows schematically a flexible bag 71 comprising a dip tube 73 inside the bag, wherein said dip tube is connected to the outside of the flexible bag by a fluid port 1 according to one embodiment of the invention. A dip tube 73 can be used for harvesting the cell culture 75 from the flexible bag 71. The dip tube 73 is in this example connected to the second fluid connection 5 of the fluid port 1. The fluid port 1 is in this example sealed to an inner wall 77 of the flexible bag 71. An opening is provided through the wall 77 mating with the first fluid connection 3 of the fluid port 1. Hereby the protection cap 11 will protect an opposing wall of the flexible bag 71 from damage. The perpendicular direction of the second fluid connection 5 compared to the first fluid connection 3 may be advantageous for the connection of the dip tube 73 and the harvesting of the cell culture. A harvest tube is connected to the first fluid connection 3 of the fluid port 1 on the outside of the flexible bag 71.

Figure 6:
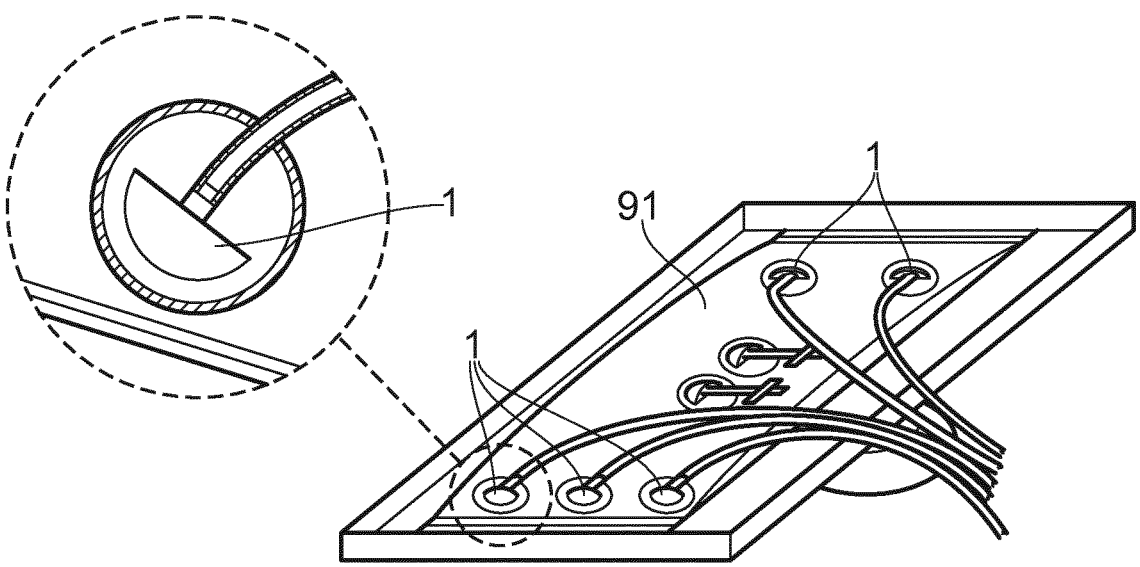
FIG. 6 shows schematically a flexible bag comprising a number of fluid ports according to one embodiment of the invention sealed to a wall of the bag.

FIG. 6 shows schematically a flexible bag 91 comprising a number of fluid ports 1 according to one embodiment of the invention. The fluid ports 1 are sealed to an outer wall of the flexible bag 91. These fluid ports 1 are used for providing fluid exchange in and out from the flexible bag. In this example the connection surfaces 13 of the fluid ports 1 are sealed to an outer wall of the flexible bag and hereby the protection caps 11 are provided on the outside of the flexible bag. The protection caps 11 will protect possible other objects from damage when they come into contact with the fluid ports 1 of the flexible bag 91. For example if many flexible bags 91 are stacked onto each other during transport or storage the protection caps 11 will reduce the risk of damage provided to flexible walls of other flexible bags. Furthermore the deviation of flow provided within the fluid ports 1 can be advantageous for connections and saving space. Tubes can be connected along the surface of the flexible bag 91 instead of perpendicular to the surface as with a normal fluid connector.

The fluid ports described and illustrated can be formed from any material, but are formed preferably from a soft plastics such as low or high density polyethylene, or polypropylene. Plasticisers to increase flexibility can be included in a moulded construction.

The invention claimed is:

1. A fluid port for providing a fluidic connection to a container, the fluid port comprising:
    a first fluid connection;
    a second fluid connection being in fluid communication with the first fluid connection;
    an intermediate fluid path connecting the first fluid connection with the second fluid connection and comprising a substantially right-angled bend;
    a protection cap covering and protecting at least the bend of the intermediate fluid path from contact with objects exterior to the container wherein the substantially right angled bend is in contact with the protection cap; and
    a connection surface, extending continuously and radially from the protection cap, and configured for sealing to a surface of the container,
    wherein said connection surface is configured to, in response to sealing together with the surface of the container, provide a fluid tight seal between the connection surface and the surface of the container surrounding the first fluid connection.

2. The fluid port according to claim 1, wherein the connection surface is disposed in the fluid port such that when the seal surrounding the first fluid connection is provided between the connection surface and the surface of the container, the first fluid connection is only accessed through an internal opening in the surface of the container surrounded by the connection surface of the fluid port.

3. The fluid port according to claim 1, wherein the protection cap is configured for covering and protecting at least the substantially right-angled bend of the intermediate fluid path from a side of the fluid port being opposite the side where the first fluid connection is provided.

4. The fluid port according to claim 1, wherein a barb is provided to the intermediate fluid path towards the second fluid connection, such that a tube can be connected to the second fluid connection of the fluid port.

5. The fluid port according to claim 1, wherein the connection surface is connected to the protection cap and wherein said protection cap is formed as a part of a dome, wherein a top position of said protection cap is provided above the bend of the intermediate fluid path and an outer periphery of the protection cap is connected to the connection surface.

6. A perfusion filter comprising the fluid port according to claim 1, wherein said connection surface of the fluid port is sealed to an outer film of the perfusion filter, wherein an opening is provided in the outer film of the perfusion filter inside the fluid tight seal surrounding the first fluid connection such that the opening mates with the first fluid connection.

7. The perfusion filter according to claim 6, wherein said outer film of the perfusion filter is EVA, Bioclear 10, Bioclear 11 or Fortem.

8. A flexible bag comprising the perfusion filter according to claim 6, wherein a tube for waste collection is connected to the second fluid connection of the fluid port, wherein the flexible bag is the container.

9. A flexible bag comprising the fluid port according to claim 1, wherein the connection surface of the fluid port is sealed to a wall of the flexible bag and wherein an opening is provided through the wall inside the surrounding seal for allowing access to the first fluid connection of the fluid port, wherein the flexible bag is the container.

10. The flexible bag according to claim 9, wherein the connection surface of the fluid port is sealed to an inner surface of the wall of the flexible bag and the protection cap is provided on the inside of the flexible bag.

11. The flexible bag according to claim 9, wherein the connection surface of the fluid port is sealed to an outer surface of the wall of the flexible bag and the protection cap is provided on the outside of the flexible bag.

12. The fluid port according to claim 1, wherein the substantially right angled bend is at least partially surrounded by the protection cap.

13. The fluid port according to claim 1, wherein the connection surface at least partially surrounds the protection cap.

14. The fluid port according to claim 1, wherein the connection surface completely surrounds the protection cap.

* * * * *